US010080816B2

United States Patent
Pillay et al.

(10) Patent No.: US 10,080,816 B2
(45) Date of Patent: Sep. 25, 2018

(54) WOUND DRESSING

(71) Applicant: UNIVERSITY OF THE WITWATERSRAND, JOHANNESBURG, Johannesburg, Gauteng (ZA)

(72) Inventors: Viness Pillay, Johannesburg (ZA); Yahya Essop Choonara, Johannesburg (ZA); Pradeep Kumar, Johannesburg (ZA); Lisa Claire Du Toit, Johannesburg (ZA); Naeema Mayet, Lenasia (ZA)

(73) Assignee: University of the Witwatersrand, Johannesburg, Johannesburg (ZA)

( * ) Notice: Subject to any disclaimer, the term of this patent is extended or adjusted under 35 U.S.C. 154(b) by 1 day.

(21) Appl. No.: 15/314,136

(22) PCT Filed: Jun. 5, 2015

(86) PCT No.: PCT/IB2015/054262
§ 371 (c)(1),
(2) Date: Nov. 28, 2016

(87) PCT Pub. No.: WO2015/186101
PCT Pub. Date: Dec. 10, 2015

(65) Prior Publication Data
US 2017/0095589 A1    Apr. 6, 2017

(30) Foreign Application Priority Data
Jun. 5, 2014   (ZA) ................................. 2014/04120

(51) Int. Cl.
*A61L 15/60* (2006.01)
*A61L 15/28* (2006.01)
*A61L 15/44* (2006.01)
*A61K 9/70* (2006.01)
*A61L 15/22* (2006.01)

(52) U.S. Cl.
CPC .............. *A61L 15/60* (2013.01); *A61K 9/703* (2013.01); *A61K 9/7007* (2013.01); *A61K 9/7092* (2013.01); *A61L 15/225* (2013.01); *A61L 15/28* (2013.01); *A61L 15/44* (2013.01); *A61L 2300/216* (2013.01); *A61L 2300/30* (2013.01); *A61L 2300/412* (2013.01)

(58) Field of Classification Search
None
See application file for complete search history.

(56) References Cited

U.S. PATENT DOCUMENTS

| | | | | |
|---|---|---|---|---|
| 2003/0104039 A1* | 6/2003 | Berthold | ........... | A61F 13/00063 424/445 |
| 2005/0137272 A1 | 6/2005 | Gaserod et al. | | |
| 2008/0069857 A1* | 3/2008 | Yeo | ........ | A61L 31/041 424/426 |
| 2014/0023692 A1* | 1/2014 | Du Toit | ............... | A61K 31/405 424/428 |

FOREIGN PATENT DOCUMENTS

| | | | |
|---|---|---|---|
| CN | 101638830 A * | 2/2010 | |
| WO | 1997/046265 | 12/1997 | |
| WO | 2001/091684 | 12/2001 | |
| WO | WO-2011004328 A2 * | 1/2011 | ............... A61K 8/64 |
| WO | 2014/039012 | 3/2014 | |

OTHER PUBLICATIONS

Lee, Kuen Yong, et al. "Electrospinning of polysaccharides for regenerative medicine." Advanced drug delivery reviews 61.12 (2009): 1020-1032.*
Tan, Huaping, et al. "Injectable in situ forming biodegradable chitosan—hyaluronic acid based hydrogels for cartilage tissue engineering." Biomaterials 30.13 (2009): 2499-2506.*
International Search Report and Written Opinion for PCT/IB2015/054262 dated Aug. 14, 2015.

* cited by examiner

*Primary Examiner* — John Pak
*Assistant Examiner* — Daniel L Branson
(74) *Attorney, Agent, or Firm* — Fish & Richardson P.C.

(57) ABSTRACT

This invention relates to a wound dressing, particularly to a stimuli responsive wound dressing comprising a lyophilized hyaluronic acid (HA) hydrogel, and a plurality of devices embedded within said lyophilized hyaluronic acid hydrogel. Each of the plurality of devices including chitosan and hypromellose and may be formed as biofilms and/or electrospun fiber mats.

16 Claims, 9 Drawing Sheets

WOUND DRESSING

FIELD

This invention relates to a wound dressing, particularly to a stimuli responsive wound dressing.

BACKGROUND

Wound dressings for application against external wounds of humans and/or animals are known. Typically, injury to the dermis of a human and/or animal results in an external wound and a bandage and/or band-aid is applied over the surface of the wound to encourage healing of said wound.

Wound treatment and management has been proven to be challenging due to the fact that various extrinsic and intrinsic factors govern significant roles during the healing process. This is particularly evident in external wounds that include damage to skin of a human or animal body.

The wound healing process typically comprises three main phases, namely: the inflammatory phase, the proliferative phase, and the remodeling phase.

The inflammatory phase prepares the wound site for healing by immobilising the wound and causing it to swell and become painful. Bleeding occurs and homeostasis is initiated, furthermore a clotting mechanism is elicited by blood platelets. The inflammatory phase also results in vasodilation and phagocytosis whereby histamines and serotonins are released.

The proliferative phase involves the proliferation of epidermal cells at the wound margin behind which actively migrating cells travel about 3 cm from a point of origin in all directions toward the wound site. This process usually occurs 2 days to 3 weeks following injury and results in granulation tissue at the wound site. Granulation is the effect of fibroblasts and macrophages providing a continuing source of growth factors necessary to stimulate angiogenesis and fibroplasias.

The final stage is known as the remodelling stage and usually begins three weeks post injury, and lasts up to 2 years. Remodelling of dermal tissue to produce greater tensile strength whereby new collagen is formed is the main aim of this phase. The principle cell type involved is the fibroblast. Collagen molecules begin to form whereby they undergo further modification and molecules begin to form in a characteristic triple helical structure.

The above phases often overlap and a standard issue wound dressing is not designed to provide in use an environment which facilitates optimal responses from the different phases. Often wound dressings are only useful during one of the abovementioned stages.

A known disadvantage in the current state of the art includes adherence of wound dressings to wounds upon removal of said wound dressing. Removal of known wound dressings often damages several layers of the dermis that have been repaired and/or are partially repaired. It is also known that in order to promote general wound healing including for example angiogenesis and connective tissue proliferation a moist wound environment should be encouraged. Often, known wound dressings dry out the wound which is disadvantageous for the wound healing process in general.

Injuries to the dermis may often result in infection, inflammation and/or sepsis. Typically, wounds are first cleaned, then various active pharmaceutical ingredients (APIs) are administered to the wound site, and finally the wound dressing is applied. Access to the various APIs and additionally the wound dressing may not always be available and a skilled medical practitioner may not always be at hand to assist in deciding which APIs need to be administered.

Furthermore, wound dressings often break and/or tear increasing the changing or replacement frequency. This disrupts the wound healing process and adds to the cost of wound treatment and/or management.

There is a need for a wound dressing that at least ameliorates one of the above mentioned disadvantages.

SUMMARY

In accordance with this invention there is provided a stimuli responsive wound dressing for application against a wound site of a human or animal body, the wound dressing comprising:
  a lyophilized hyaluronic acid (HA) hydrogel; and
  a plurality of devices embedded within said lyophilized hyaluronic acid hydrogel, each device including chitosan and hypromellose,
  wherein said lyophilized hyaluronic acid hydrogel depolymerizes upon contact with hydroxyl radicals from an inflammatory response present at the wound site in order to release the plurality of embedded devices into the wound site, and
  wherein said lyophilized hyaluronic acid hydrogel absorbs water and/or exudates facilitating the maintenance of a moist wound site which promotes wound healing.

The lyophilized hyaluronic acid hydrogel may further comprise alginate, the alginate in use absorbs water and/or exudates facilitating the maintenance of a moist wound site which promotes wound healing. The alginate may generally in use also act as a deodorizer. Preferably, the alginate is sodium alginate.

The lyophilized hyaluronic acid hydrogel may further comprise a first crosslinking agent. The first crosslinking agent may be selected from, but not limited to, a group of dihydrazides including: adipic dihydrazide (ADH), dithiobis (propanoic dihydrazide) (DTP), dithiobis(butyric dihydrazide) (DTB), tyrosine and tyrosine hydrazide whereby thiol groups and disulfide linkages can be formed upon crosslinking, and/or further coupling by carbodiimides. Preferably, the first crosslinking agent may be adipic dihydrazide (ADH).

Each of the plurality of devices may further comprise an active pharmaceutical ingredient (API). The API may be at least one plant phytochemical selected from, but not limited to, the following group: curcumin, farnesol, benzoic acid, eugenol and cinnamic acid. The API may be at least one plant extract selected from, but not limited to, the following group; *Thymus vulgaris* (thyme), *Rosmarinus officinalis* (rosemary), *Syzygyum joabolanum* (jambolan), *Salvia officinalis* (sage). In a preferred embodiment of the invention, the API may be curcumin.

Each of the plurality of devices may further comprise a second crosslinking agent selected from, but not limited to, iridoid compounds and/or derivatives of iridoid compounds. The second crosslinking agent may selected from the following group: genipin and chromium ascorbate, in use the crosslinking agent crosslinks the chitosan. In a preferred embodiment of the invention, the second crosslinking agent is genipin.

Each of the plurality of devices may further comprise citric acid.

The devices may be formed to be biofilms and/or electrospun fiber mats.

In an embodiment of the invention wherein the devices are prepared as biofilms, the biofilms may further comprise glycerine.

In an embodiment of the invention wherein the devices are prepared as electrospun fiber mats, the fiber mats may further comprise at least one of the following group: polyethylene oxide (PEO), polyvinyl chloride (PVA) and Tween 80.

The wound dressing may further comprise a backing layer upon which the lyophilized hyaluronic acid (HA) hydrogel is layered so as to form a bi-layered wound dressing, in use, the backing layer faces away from the wound site and facilitates unidirectional release of the plurality of devices.

The backing layer may be a hydrogel formulation. The backing layer may comprise alginate and/or polyacrylic acid. The backing layer may further include a platisizer, preferably the plastisizer may be glycerol. The backing layer may further include an anti-foaming agent.

There is further provided for a wound dressing substantially as herein described, illustrated and/or exemplified with reference to the accompanying examples and/or diagrammatic drawings.

BRIEF DESCRIPTION

Embodiments of the disclosure will be described below by way of example only and with reference to the accompanying drawings in which.

Figure 8A:
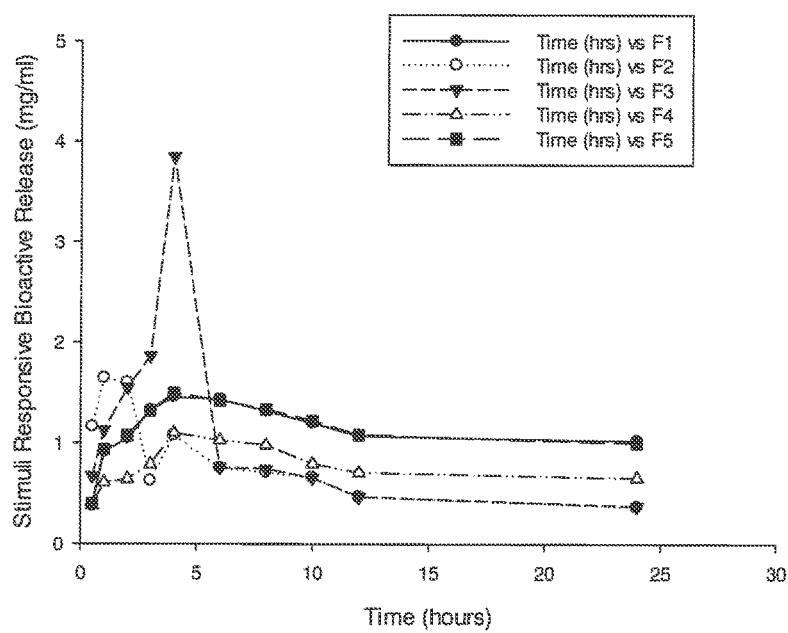
Figure 8B:
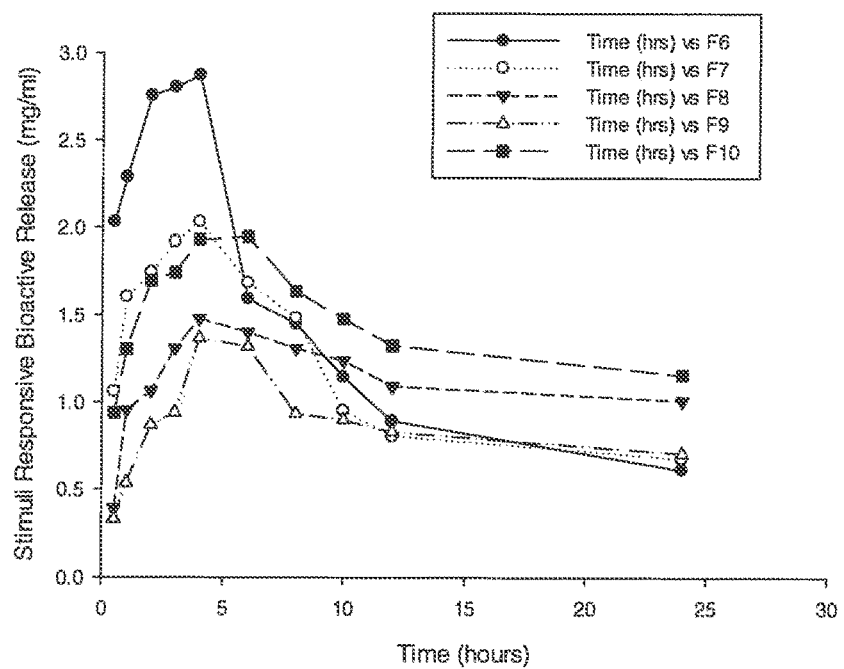
Figure 8C:
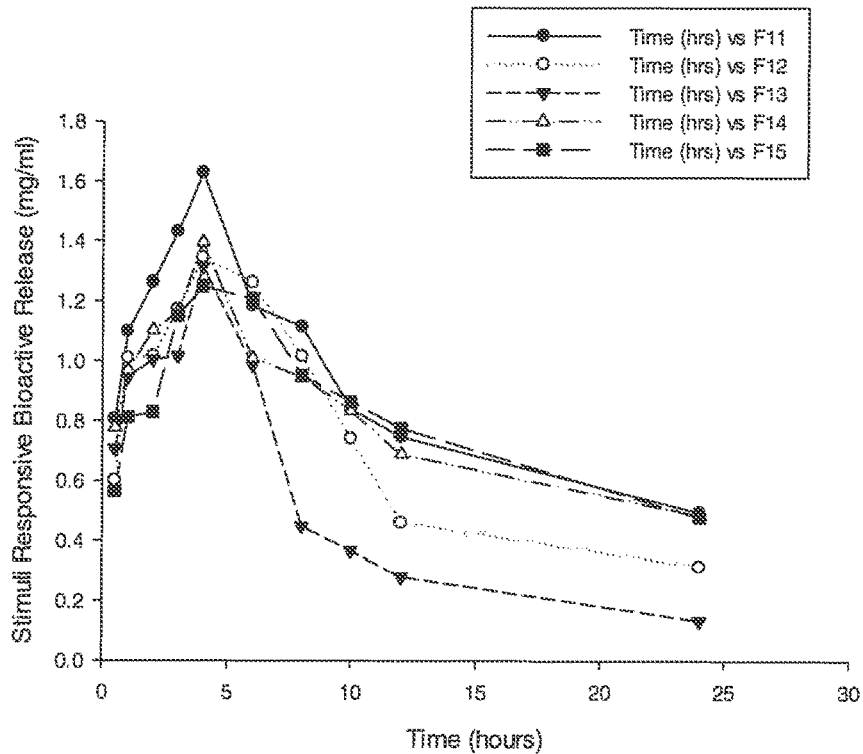
Figure 9:
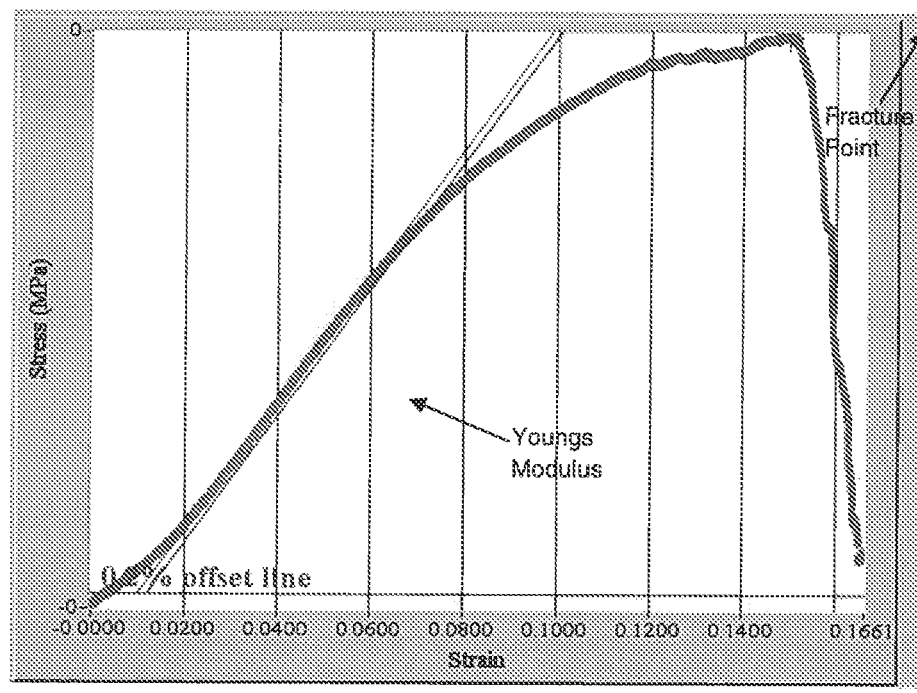

FIG. 8 shows in vitro bioactive release profiles of lyophilized HA hydrogel Formulations 1-15 further including electrospun fiber mats containing API; (a) shows HA hydrogel formulations F1-F5, (b) shows HA hydrogel formulations F6-F10, and (c) shows HA hydrogel formulations F11-F15, all Formulations included Optimized drug loaded electrospun fiber mats; and FIG. 9 depicts a standard stress-strain profile for HA hydrogel Formulation 2 that is obtained upon nanotensile mapping depicting a fracture point and youngs modulus from the graph.

DETAILED DESCRIPTION

Specific, but non-limiting embodiments of the invention will now be described.

In accordance with this invention there is provided a stimuli responsive wound dressing for application against a wound site of a human or animal body. The wound healing process typically comprises three main phases, namely: the inflammatory phase, the proliferative phase, and the remodeling phase, and the wound dressing according to the invention seeks to provide healing during at least one of, but preferably all three, the wound healing phases.

The wound dressing comprises a lyophilized hyaluronic acid (HA) hydrogel, and a plurality of devices embedded within said lyophilized hyaluronic acid hydrogel, each device including chitosan and hypromellose.

In use, the lyophilized hyaluronic acid hydrogel of the wound dressing depolymerizes upon contact with hydroxyl radicals from an inflammatory response present at the wound site in order to release the plurality of embedded devices into the wound site, and the lyophilized hyaluronic acid hydrogel absorbs water and/or exudates facilitating the maintenance of a moist wound site which promotes wound healing. This generally occurs during the inflammation phase. During the proliferation phase HA provides for the promotion of proliferation and regeneration of cells at the wound site. During the remodeling phase HA provides for facilitates cell migration to aid tissue remodeling. As such, the HA component contributes to healing during all three of the healing phases.

The chitosan of each device aids homeostasis of the wound site during the inflammation phase, promotes differentiation, re-epithelisation and fibroplasias during granulation associated with the proliferation phase, and facilitates decreased hypertophic scar formation during the remodeling phase. As such, the chitosan of each device contributes to healing during all three of the healing phases.

The hypromellose of each device promotes and/or facilitates angiogenesis during the proliferation phase of wound healing.

The lyophilized hyaluronic acid hydrogel typically further comprises alginate. The alginate in use absorbs water and/or exudates facilitating the maintenance of a moist wound site which promotes angiogenesis and wound healing. The alginate also act as a deodorizer. Preferably, the alginate is sodium alginate.

The lyophilized hyaluronic acid (HA) hydrogel generally further comprises a first crosslinking agent. The first crosslinking agent may be selected from, but not limited to, a group of dihydrazides including: adipic dihydrazide (ADH), dithiobis(propanoic dihydrazide) (DTP), dithiobis(butyric dihydrazide) (DTB), tyrosine and tyrosine hydrazide whereby thiol groups and disulfide linkages can be formed upon crosslinking, and/or further coupling by carbodiimides. Preferably, the first crosslinking agent may be adipic dihydrazide (ADH). Preferably, the first crosslinking agent is adipic dihydrazide (ADH) and crosslinking with HA produces a HA-ADH hydrogel complex.

Typically, each of the devices each include an active pharmaceutical ingredient (API) to treat the wound site in order to promote wound healing. At least one, but several APIs, might be included into the devices. The API may be at least one plant phytochemical selected from, but not limited to, the following group: curcumin, farnesol, benzoic acid, eugenol and cinnamic acid. The API may be at least one plant extract selected from, but not limited to, the following group; *Thymus vulgaris* (thyme), *Rosmarinus officinalis* (rosemary), *Syzygyum joabolanum* (jambolan), *Salvia officinalis* (sage). In a preferred embodiment of the invention, the API may be curcumin In a preferred embodiment of the invention described in the examples below, the API is curcumin. During the inflammation phase curcumin provides anti-inflammatory activity, anti-oxidant activity and facilitates TGF-β1 formation. During the proliferation phase curcumin facilitates cell proliferation, induction of growth factors and granulation tissue formation.

Each of the plurality of devices may further comprise a second crosslinking agent selected from, but not limited to, iridoid, iridoid compounds and/or derivatives of iridoid or iridoid compounds. The second crosslinking agent may selected from the following group: genipin and chromium ascorbate, in use the crosslinking agent crosslinks the chitosan. In a preferred embodiment of the invention, the second crosslinking agent is genipin.

Each of the plurality of devices may further comprise citric acid. The citric acid in use dissolves the chitosan during the formation of the plurality of devices, as will be explained in greater detailed in the examples hereunder. The citric acid provides anti-microbial activity in use during the inflammation phase, and aids in layer granulation during the proliferation phase. The Applicant found citric acid to be especially advantageous in not only providing a dissolution media for chitosan, but also providing wound healing properties in use.

The devices may be formed to be biofilms and/or electrospun fiber mats. The preparation procedures for both biofilm and electrospun fiber mat embodiments are explained in greater detail in the examples below.

In an embodiment of the invention wherein the devices are prepared as biofilms, the biofilms may further comprise glycerine. Biofilm devices are typically formed such that chitosan and hypromellose form an interpenetrating polymer network (IPN).

In an embodiment of the invention wherein the devices are prepared as electrospun fiber mats, the fiber mats further comprise at least one of the following group: polyethylene oxide (PEO), polyvinyl chloride (PVA) and Tween 80. PEO has emollient properties when applied to skin and/or hair, it also has binding, water retentive and film forming properties, is non-ionic and has good lubricating properties.

The wound dressing generally further comprises a backing layer upon which the lyophilized hyaluronic acid (HA) hydrogel is layered so as to form a bi-layered wound dressing. In use, the backing layer faces away from the wound site and facilitates unidirectional release of the plurality of devices.

The backing layer is typically a hydrogel formulation. The backing layer typically comprises alginate and/or polyacrylic acid. The backing layer may further include a platisizer such as glycerol. The backing layer may further include an anti-foaming agent.

EXAMPLES

Materials and Methods
Materials

All experiments conducted employed the use of chitosan, medium molecular weight poly(D-glucosamine) deacetylated chitin obtained from Sigma Aldrich Chemie GmbH, Steinheim, Germany, Hypromellose-hydroxymethylcellulose 2910 obtained from Sigma Aldrich Chemie GmbH, Steinheim, Germany, citric acid ACS reagent ≥99.5%, mw 192.12 g/mol obtained from Sigma Aldrich Chemie GmbH, Steinheim, Germany, genipin ≥98% (HPLC) powder with a molecular weight of 226.23, curcumin obtained from Sigma Aldrich Chemie GmbH, Steinheim, Germany In addition all electrospinninng experiments conducted employed the use of polymers PVA-mowiol® 4-88 with a molecular weight of 31000 andPEO-Polyox™, WSR 303 obtained from Sigma Aldrich Chemie GmbH, Steinheim, Germany Tween 80 uniLAB® (Merck Chemicals (Pty) Ltd, Wadeville, Gauteng, RSA) was incorporated to improve the electrospinnability of the nanofibres.

Glycerol, Tween 80 Associated Chemical Enterprises Pty Ltd. (Southdale, South Africa), Silicon (BDH, VWR International Ltd, London, UK), Parrafin Liquid (Saarchem Wadeville, Gauteng, South Africa), Sodium alginate, Polyacrylic acid, Hyaluronic acid, Adipic Dihydrazide (ADH) (Sigma Aldrich Chemie GmbH, Steinheim, Germany) All other materials used were of analytical grade and used as received.

Preparation of Lyophilized Hyaluronic Acid Hydrogel

A hyaluronic acid (HA) hydrogel was produced by solution polymerisation using deionised water as the solvent. Further crosslinking was undertaken by preparing a hyaluronic acid-adipic dihydrazide complex as a hydrogel. A hyaluronic acid solution (5 g/ml) was crosslinked with adipic dihydrazide (ADH) under continuous stiffing using a magnetic stirrer (Luo et al., 2000). Sodium alginate dispersed within deionised water was added to the HA-ADH solution to form a complex hydrogel.

The Formulations 1-15 of HA hydrogel were statistically derived from a Box-Behnken Design template as follows:

TABLE 1

Box-Behnken Design Template of the 15 statistically derived formulations for the design of the lyophilised hyaluronic acid (HA) hydrogel

| Experimental Formulation | Alginate (% w/v) | Hyaluronic Acid (% w/v) | Adipic Acid Dihydrazide (% w/v) |
|---|---|---|---|
| 1 | 2.75 | 0.5 | 0.13 |
| 2 | 2.75 | 0.7 | 0.16 |
| 3 | 4.5 | 0.5 | 0.16 |
| 4 | 4.5 | 0.3 | 0.13 |
| 5 | 2.75 | 0.5 | 0.13 |
| 6 | 2.75 | 0.3 | 0.16 |
| 7 | 1 | 0.3 | 0.13 |
| 8 | 2.75 | 0.5 | 0.13 |
| 9 | 2.75 | 0.7 | 0.1 |
| 10 | 1 | 0.5 | 0.1 |
| 11 | 1 | 0.7 | 0.13 |
| 12 | 4.5 | 0.5 | 0.1 |
| 13 | 2.75 | 0.3 | 0.1 |
| 14 | 4.5 | 0.7 | 0.13 |
| 15 | 1 | 0.5 | 0.16 |

Preparation of Biofilm Devices

The present invention encompasses the use of chitosan (CHT) as a starting material. To ensure optimal dissolution, an aqueous acidic solution comprising of a 5% (50 mg/ml) citric acid is prepared as a solvent medium. The chitosan used is of medium molecular weight and uncrosslinked. The concentration of chitosan in this invention varies from 1% (10 mg/ml) to 3% (30 mg/ml) and plays a crucial role in the fabrication of a wound healing film. Concentrations at a lower range tend to provide lower tensile strength and are easily degradable when exposed to an aqueous medium whereas at a higher concentration range films will show enhanced physic-mechanical properties that tend to degrade at a much slower rate. The preferred concentration of chitosan to ensure an Optimised Film is 3% (30 mg/ml) relative to the addition of biopolymers within the scope of this invention. Crosslinking of chitosan can be obtained by the addition of a crosslinking agent such as genipin dissolved in deionised water in order to form an interpenetrating polymer network (IPN) blend. Genipin a crosslinker was used at concentrations ranging from 0.01% (10 mg/10 ml) to 0.05% (50 mg/10 ml), as above 0.05% rapid degradation and tearing of films are observed. For the aforementioned invention a low concentration of 0.01% is required in order to obtain optimal crosslinkage. Aqueous solutions of both hypromellose and curcumin were formulated at concentrations of 0.4%(4 mg/ml) and 1%(10 mg/ml) respectively. This is then added to the crosslinked chitosan solution with 1ml of glycerine. The solution is then allowed to stir overnight to optimally form an interpenetrating polymer network (IPN) blend and poured into film moulds made with the use of parafilm at the desired thickness (10 ml). Film moulds are then placed in fumehood with the onset of a fan and allowed to air dry.

Preparation of Electrospun Fiber Mat Devices

This invention encompasses the electrospinning of polymer solutions (as described above) but modified to favour electrospinning conditions. The addition of bioactives and reagents chitosan, citric acid, genipin, hypromellose and curcumin is carried out as described above for the biofilms with the addition of 10% PVA(dissolved in deionised water) and 2% PEO (dissolved in 40% ethanol and 60% deionised water). 1 ml of a surfactant, Tween 80 is also incorporated. This is blended until homogenous at equal ratios of polymer solution: PEO:PVA and then electrospun which involves the application of a voltage of 20 kv supplied by Glassman high voltage inc,(High Bridge N.J. USA) to the bio solution via a pipe attached at one end to a 10 ml syringe that is inserted in the slot provided by the pump (Chemyx Inc syringe infusion pump) to ensure a flow rate of 1500 μl/h and attached to a 21G needle at the other end mounted at a distance of 37.5 cm from the collecting surface. The solution will be fed into the syringe and allowed to run whereby nanofibres will be collected on an aluminium foil attached to the collecting surface whereby a nanofibrous mat can be formed.

Biofilm devices and electrospun fiber mats were produced following a statistically derived Box-Behnken Design template as indicated in Table 2 below:

TABLE 2

Box-Behnken Design Template for biofilm and electrospun fiber mat devices

| Formulation No. | Chitosan (% w/w) | Genipin (% w/w) | Hypromellose (% w/w) |
| --- | --- | --- | --- |
| 1 | 3 | 0.25 | 1.6 |
| 2 | 1 | 0.25 | 0.4 |
| 3 | 3 | 0.1 | 1 |
| 4 | 2 | 0.1 | 1.6 |
| 5 | 1 | 0.25 | 1.6 |
| 6 | 2 | 0.25 | 1 |
| 7 | 2 | 0.4 | 0.4 |
| 8 | 3 | 0.25 | 0.4 |
| 9 | 2 | 0.25 | 1 |
| 10 | 3 | 0.4 | 1 |
| 11 | 1 | 0.4 | 1 |
| 12 | 1 | 0.1 | 1 |
| 13 | 2 | 0.4 | 1.6 |
| 14 | 2 | 0.1 | 0.4 |
| 15 | 2 | 0.25 | 1 |

Synthesis and Formation of a Backing Layer for Attachingly Layering onto the Lyophilized Hyaluronic Acid (HA) Hydrogel The film casting method was employed whereby various concentrations of alginate was dissolved in solvent, together with deionised water and polyacrylic acid. A hydrogel was subsequently formulated by sequential blending of the polymer solutions, followed by the addition of the plasticizer glycerol at a concentration of 2:1 (polymer: plasticizer). Thereafter 1 drop of antifoaming agent silicon was added to the solution. Solution blends were allowed to stir on a magnetic stirrer until a homogenous solution was formed. The optimum amount of each blend (+/−10 mL) was poured into a mould composed of parafilm, rectangular in shape (710 mm×260 mm) lubricated with liquid paraffin and cast in film form by solvent evaporation at room temperature with the use of a fumehood under the influence of continuous airflow. After being dried, membrane films was removed from the fumehood and parafilm and utilised as a backing layer for the wound dressing according to the invention.

Formation of a Wound Dressing Including Electrospun Fiber Mat Devices

Figure 1:
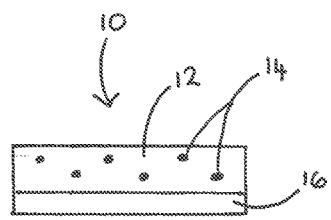
FIG. 1 shows a cross-sectional portion of the wound dressing according to the invention.

A hyaluronic acid (HA) hydrogel was produced by solution polymerisation using deionised water as the solvent. Further crosslinking was undertaken by preparing a hyaluronic acid-adipic dihydrazide complex as a hydrogel. A hyaluronic acid (HA) solution (5 g/ml) was crosslinked with adipic dihydrazide (ADH) under continuous stiffing using a magnetic stirrer (Luo et al., 2000). Sodium alginate dispersed within deionised water will be added to the HA-ADH solution to form a complex hydrogel whereby wound healing nanofibrous mats were suspended in the gel and immediately frozen. The above system will then be lyophilised to form a stimuli responsive matrix reserviour that can be ajoined to the backing layer as described above. The wound dressing 10 according to the invention is shown in cross-section in FIG. 1 and shows a HA hydrogel 12 having embedded therewith devices 14 of an electrospun fiber mat formulation, and further wherein the HA hydrogel is layered onto a backing layer 16.

Characterization of Biofilms and Electrospun Fiber Mats

Fourier Transform Infrared Spectroscopy

Figure 2A:
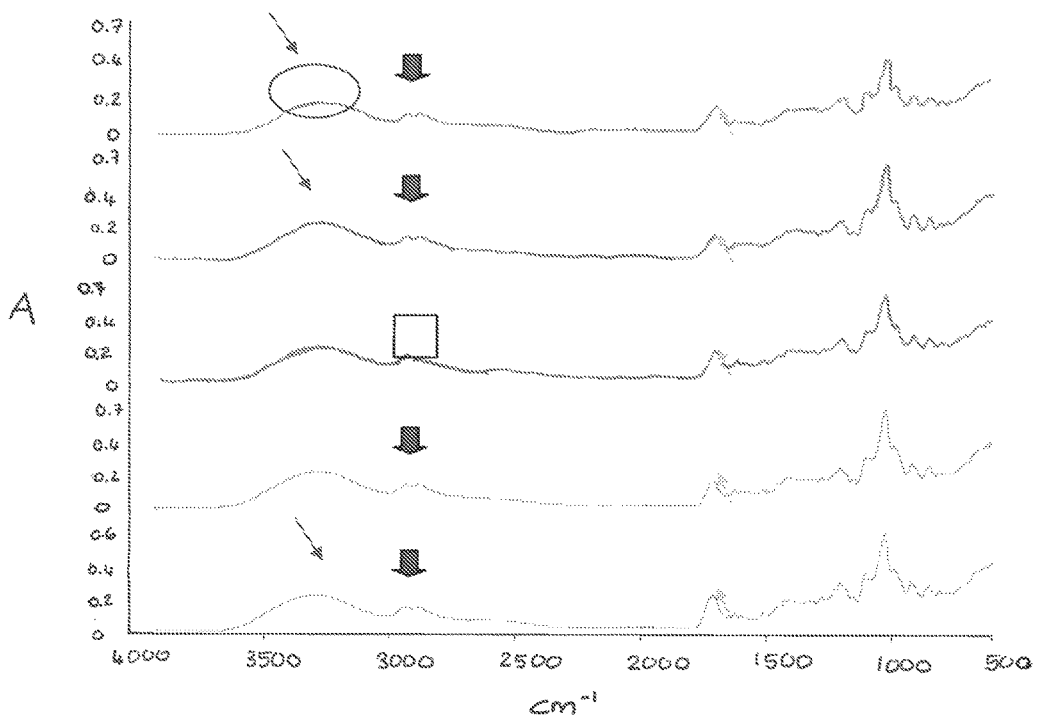
FIG. 2 (a) shows FTIR spectra of semi-IPN biofilm devices—A (Film 1), B (Film 2), C (Film 5), D (Film 9) and E (Film 10); and (b) shows an FTIR spectrum of electro spun fiber mat (nanofibrous mat) of Formulation 13.
Figure 2B:
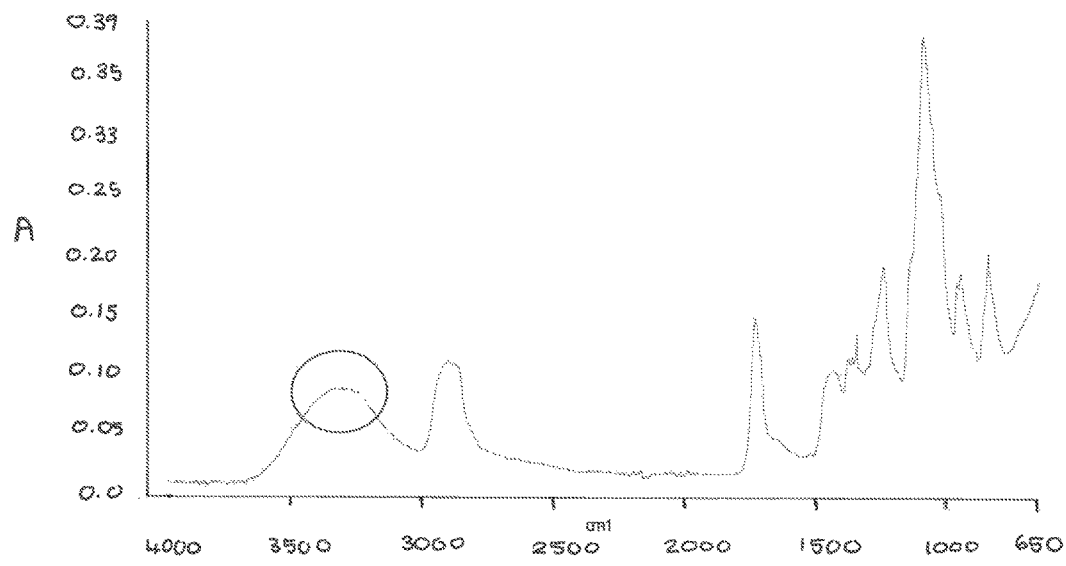

Structural changes within the films that took place during degradation was collected using attenuated total reflectance Fourier transform infrared spectroscopy ATR-FTIR analysis which identifies absorption bands based on vibrational molecular transitions which characterize complex interactions occurring within bioactive polymer exchanges. A PerkinElmer® Spectrum 100 Series FT-IR Spectrometer fitted with a universal ATR Polarization Accessory (PerkinElmer Ltd., Beaconsfield, UK) was employed and Spectra over the range 4000-625 $cm^{-1}$, with a resolution of 4 $cm^{-1}$ and 32 accumulations was recorded. FIG. 2a and b show representative spectra of FTIR for (a) polymer biofilm devices and the effects at different concentrations and (b) electrospun fiber mats being nanofibrous mats. FIG. 2a shows FTIR spectra of semi-IPN biofilm devices, from top to bottom, A (Film 1), B (Film 2), C (Film 5), D (Film 9) and E (Film 10). FIG. 2b shows FTIR spectra of electro spun fiber (nanofibrous mat) of Formulation 13.

Physical and chemical interactions occurring on interpenetrating network (IPN) formation of various concentration polymer blends were evaluated using FTIR, which determines the degree of modification within the native polymer. The crosslinking within the films (FIG. 2a) was characterized by the change in colour from yellow due to bioactive incorporation to a dark deep green when crosslinked with genipin, furthermore the disappearance of a peak when crosslinked, at a wavelength of 1223.62 $cm^{-1}$ representative of C—O stretching within the aromatic ring indicates the formation of a crosslinking bridge at the aromatic site of genipin with chitosan thus the formation of a crosslinked network. Furthermore O—H stretching occurs indicated by the large broad bend and a shift in wavelength and absorbance is observed from 3260.11 to 3278.79 cm$^{-1}$ and 0.34 to 0.35A respectively when crosslinked suggesting an increase in conjugation and intensity thus improving the stability and physic-mechanical properties of the film. On observation of the FTIR spectra it can further be deduced that a change in polymer concentrations resulted in a slight change within the spectra. A broad strong band representing hydrogen bonding for O—H stretching within the range of 3200 cm$^{-1}$ and 4000 cm$^{-1}$ can be observed with all biofilms. A shift within the spectrum varies with the degree of crosslinkage. Film 10 shows a wavelength at 3923.54 cm$^{-1}$ whereas a wavelength of 3289.37 cm$^{-1}$ and 3268.02 cm$^{-1}$ is present in Film 1 and 2 respectively (shown using arrows in the figure) characteristic to the bioactive curcumin indicating that an increase in crosslinker concentration resulted in a shift to a greater wavelength thus promoting conjugation and bond formation. In addition the absence of a peak at the wavelength of 1281.98 cm$^{-1}$ representative of the presence of an additional amino group in Film 1, indicates no presence of free amino groups as seen with Film 2, 5, 9 and 10. This could be due to low chitosan polymer concentration and more crosslinker thus the formation of steric hindrance ensuring no presence of free amino groups. Film 5 shows the presence of a wavelength at 1980.69 cm$^{-1}$ (indicated by the block in the figure) which is not characteristic of any polymer entity but representative of the formation of C=C conjugation asymmetrical stretch and occurs when an intermediate amount of polymer entities are used thus the formation of intermolecular bonds.

Interpenetrating polymer network formation resulted in significant differences in infrared absorption frequencies of the final product in relation to the original compounds. Network formation resulted in a change in the vibrational energy and frequency thus the presence of skeletal vibrations at wavelengths of 2937.54 cm$^{-1}$ and 2881.46 cm$^{-1}$ (highlighted by arrows) which are characteristic of C—H stretching and a wavelength of 1712.30 cm$^{-1}$ (highlighted by arrows) characteristic of C=O stretching are noted. C—H bending within the aromatic ring is seen at wavelengths 921.85 cm$^{-1}$, 808.96 cm and 621.69 cm$^{-1}$ related to the incorporation of a C—N group in place of the C—O group within the ring due to crosslinking. C—N stretching is also present at the wavelength of 1318.16 cm$^{-1}$ and 1280.60 cm$^{-1}$. These peaks occur at higher vibrational frequencies and are associated with the degree of polymer network formation as well as crosslinking resulting in a change within the structural environment. As the concentration of crosslinker was increased so too did the intensity of the band formation, resulting in stretching and conjugation within the structure and bending between C—H bonds in the aromatic ring. Formulations displaying greater band intensities correspond to a higher degree of crosslinking, hence it can be deduced that the degree of interpenetrating polymer network formation is affected largely by the polymers and crosslinker concentration.

Comparisons were conducted between the spectra of both biofilms and electrospun (nanofiber) mats and it is was observed that the wavelengths and absorbance of the nanofibres mats as seen in FIG. 2b was much greater than those in FIG. 2a representative of the biofilms. This suggests that nanofibres present greater stability and physico-mechanical properties as an increase in the wavelength and absorbance represents greater intensity and conjugation between bonds. By way of illustration, the first broad peak in both figures (circled) show O—H stretching representative of hydrogen bonded phenols in their structures however it occurs at a greater wavelength of 3305.03 cm$^{-1}$ in the nanofibres (FIG. 2b) and 3289.15 cm$^{-1}$ in the biofilms (FIG. 2a) thus representing greater conjugation and subsequent stability.

Morphological Observations of Biofilm and Electrospun Fiber Mat Devices

Figure 3:
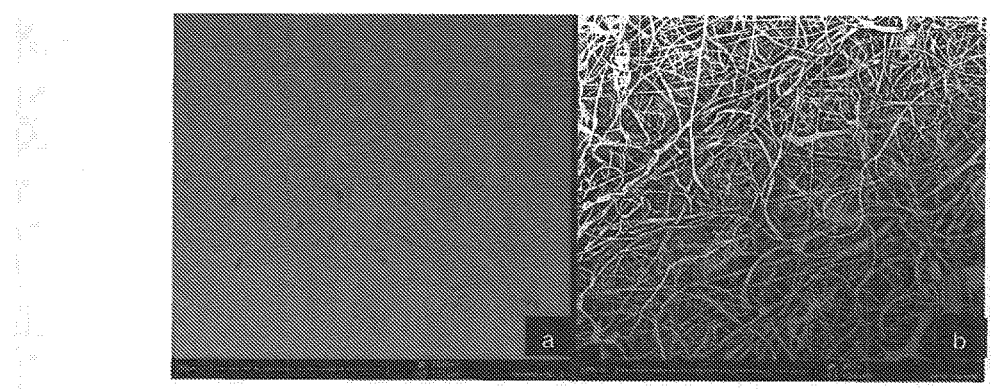
FIG. 3 shows scanning electron microscopy images of a) biofilm and b) electrospun fiber mat devices.

Surface topographical structure of the dry biopolymer films was observed using a SEM (Phenom™, FEI Company, Hillsboro, Oreg., USA). Samples were cut from biofilms and mounted into metal stubs whereby samples were gold coated with an in-house SPI-Module Sputter Coater (SPI Supples, Division of Structure Probe Inc., West Chester, Pa., USA). SEM analysis permits visualisation of porosity, surface roughness and particle size of biofilms. FIG. 3 shows scanning electron microscopy images of a) biofilm and b) nanofibres (electrospun fiber mat) devices.

Scanning electron miscroscopic evaluation revealed the surface morphology of both films and nanofibres. Films (a) tend to be flat, smooth, and continuous with the presence of pores randomly situated. Nanofibres (b) show the random orientation of fibres that are cylindrical and solid in shape and have the capability to mimic the topographical alignment of native skin tissue. Thus the healing function of b would be optimised to a greater extent than a.

Figure 4:
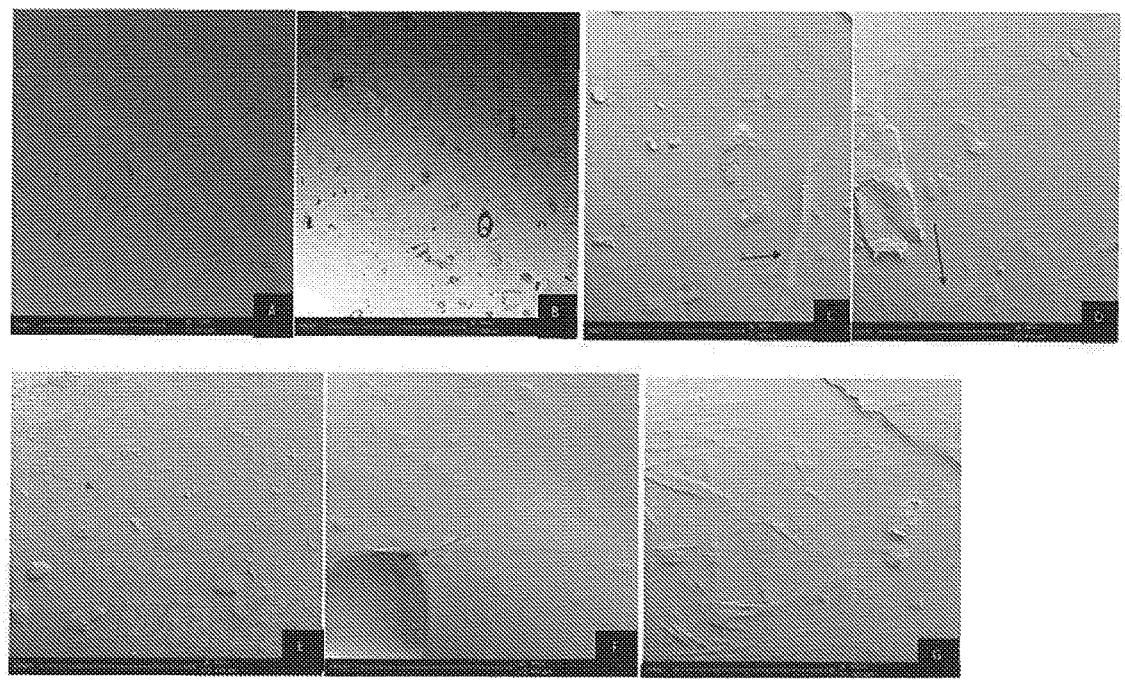
FIG. 4 shows scanning electron micrographs of s-IPN film devices (A and B), Optimized Films, (C) Film 1, (D) Film 2, (E) Film 5, (F) Film 9, and (G) Film 10.

FIGS. 4a-g demonstrates the SEM images of the semi-IPN films and the difference in surface morphologies of the films prepared using various polymer and crosslinker concentrations. Zhao et al and Bhuvaneshwari et al have reported that the surface morphology of pure chitosan films is relatively smooth, non-porous, flat and homogenous. However with the introduction of a polymer IPN, the addition of bioactives and crosslinking modification to the surface revealed a slightly rough surface texture with the existence of pores and cracks in some instances, confirming a porous network microstructure which is one of the essential features required to optimise gaseous exchange at the wound site. Porous structures were clearly observed in all micrographs of films but the pore size and shape differed as shown in FIG. 4e (Film 5) which had a slightly more rough surface topology with pores that were elongated and small in shape, whereas Film 10 (FIG. 4g) showed a surface morphology with a more fibrous like structure, pores tend to be long, larger and rod-like in shape. Film 9 (FIG. 4f) showed pores that are much larger and clearly hollow with a definite border, whereas Film 1 (FIG. 4c) and Film 2 (FIG. 4d) showed a similar surface morphology with randomly orientated pores that are indefinite in size, shape and structure with the presence of a few cracks on the film surface. These differential surface features were attributed to the different polymer concentration and degree of crosslinking in the respective films. Film 9 (FIG. 4f) and Film 10 (FIG. 4g) have the highest quantity of crosslinker relating to the greatest degree of crosslinking therefore these films exhibit larger pores. However distinguishing features of pores of the various films such as those in Film 9 (FIG. 4f) and Film 10 (FIG. 4g) could be accounted to a lower concentration of chitosan (CS) at 3% and higher CS concentrations of 1% been used in Film 9 (FIG. 4g) and Film 10 (FIG. 40, respectively. A lower degree of crosslinking results in cracks within the surface due to poor tensile properties as observed for Film 2 (FIG. 4d). When both the crosslinker and CS were used in intermediate quantities in films the pores were notably smaller and the surface topology was rougher relating to the percentage crystallinity as observed in Film 5 (FIG. 4e). FIG. 4 shows scanning electron micrographs of s-IPN films (A and B) Optimized Films, (C) Film 1, (D) Film 2, (E) Film 5, (F) Film 9, (G) Film 10.

The Optimized Films were prepared under ambient room conditions from statistically derived superlative concentrations as indicated in Table 3 below. The aqueous polymeric solution was prepared by dissolving chitosan with citric acid (5%: 50 mg/ml). An aqueous hypromellose solution was then added followed by the crosslinker genipin. Lastly the bioactive curcumin (1%:10 mg/ml) was added.

For Optimized nanofibrous mats the components of Table 3 were then blended with electroconductive agents PVA (10%) in deionised water and PEO (2%) in 40% ethanol and 60% deionised water at a ratio of 1:1:1 respectively. Lastly 1.5 mg of NaCl and 1 mL of polyoxyethylene sorbitan monooleate was added. The polymeric solution was then processed through a pump (Chemyx Inc syringe infusion pump) attached to the electrospinner (Glassman high voltage Inc, (high bridge N.J. USA)) and a voltage of 20 kV was applied. Nanofibres were collecting surface on a collecting surface.

TABLE 3

Optimized film and nanofibers included the following components

| | Chitosan (% w/w) | Genipin (% w/w) | Hypromellose (% w/w) |
|---|---|---|---|
| Optimised Formulation | 3 | 0.1 | 0.4 |

Figure 5:
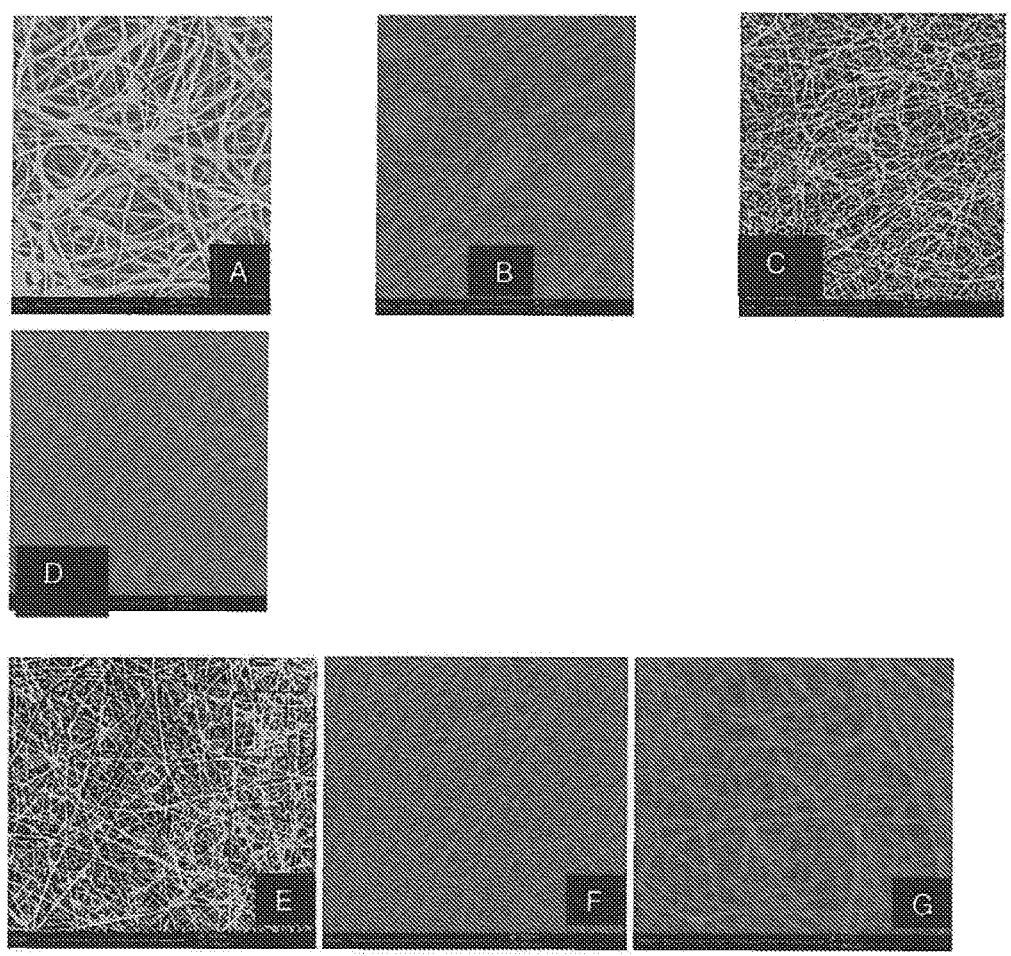
FIG. 5 shows scanning electron microscopic profiles of (A) NF 3, (B) NF 2, (C) NF 4, (D) NF 5, (E) NF 9, (F) NF 6 and (G) NF 15, wherein NF is an electrospun fiber mat also termed herein a nanofibrous mat.

Profiles obtained by scanning electron microscopic of nanofibrous mat devices (electrospun fiber mat devices) and subsequent evaluation revealed the presence of fibres that were randomly orientated, cylindrical, solid and varying in diameter. Furthermore fibres presented with a porous surface structure and characteristics were dependent on both polymer and crosslinker concentrations. A porous surface morphology is required for the process of wound healing and will be necessary for skin reconstitution. This is favourable for the process of homeostasis, adequate nutrient and gaseous exchange as well as aiding the process of proliferation and cellular infiltration. The generation of porous sites are made possible for cellular in growth by the formation of nanofibres orientated in a random loose manner as can be clearly seen in the images displayed in FIG. 5. The presence of nanofibres loosely located over one another in a arbitrary manner provides an overall network architecture that best mimics the native extra cellular matrix (ECM) of the skin thus potentiating cellular regenerative effects (Chong et al., 2007). The formation of nanofibres by electrospinning has gained much attention, however several challenges are faced as various systematic parameters need to be considered. Uniformity, size and diameter of nanofibre morphology are greatly affected and dependent on parameters such as the solution viscosity. A solution with a higher viscosity results in nanofibres with a larger diameter, prevents the formation of beads and beaded fibres as well as the presence of junctions and bundles which indicate wet fibres on reaching the collector (Haghi and Akbari., 2007; Pham et al., 2006). FIG. 5b reveals the presence of nanobeads (circled) that are large and spherical in shape and are due to low polymeric chitosan and hypromellose concentrations used, crosslinked to a lesser degree thus depicting Rayleigh instability with regards to solution viscosity. As polymeric concentrations are increased (i.e.: chitosan from 1% to 3% and Hypromellose from 0.4 to 1.6%) so does the instability decrease thus resulting in fibres that demonstrate uniformity, larger diameters as well as the absence of nanobeads as can be seen in FIG. 5a, FIG. 5c and FIG. 5g. The addition of a crosslinker contributed to an adjustment within the nanofibrous morphology thus substantiating the physicomechanical properties of the system. Crosslinking within nanofibrous mats resulted in a dense, narrowly packed structure seen in FIG. 5d, FIG. 5e and FIG. 5f due to the contraction of nanofibres by genipin. In addition to improving physicomechanical properties of the system, crosslinking also prolongs the release of bioactives due to the change brought about to the structure morphology decreasing surface area and the fusion occurring between individual fibres (Shaikh et al., 2012) as a result of crosslinking as is clearly depicted in FIG. 5e (rectangular blocks). FIG. 5 shows scanning electron microscopic profiles of (A) NF 3, (B) NF 2, (C) NF 4, (D) NF 5, (E) NF 9, (F) NF 6 and (G) NF 15, wherein NF is an electrospun fiber mat also termed herein a nanofibrous (NF) mat.

Advanced Differential Scanning Calorimetry of Biofilms and Electrospun Fiber Mats DSC measurements were taken using an Advanced DSC (TMDSC/ADSC) (Mettler Toledo DSC-1 STAR$^e$ System, Schwerzenback, ZH, Switzerland) on samples having a weight between 7-10 mg at a heating rate of 10° C./min from −10 to 350° C. under nitrogen atmosphere. Weighed samples were placed in a covered aluminium sample holder with a central pin hold. Calibration of the DSC modulus was done in respect to enthalpy and temperature. Thermoanalysis of the samples was carried out in regards to glass transitions, melting points, chemical reactions and phase change temperatures of polymeric systems. FIG. 6 shows DSC results for (a) the biofilm devices and (b) the electrospun fiber mats. FIG. 6 shows DSC schematic of (a) biofilm devices— showing A (Film 6), B (Film 11), C (Film 3, D (Film 10) and E (Film 2); and (b) electrospun fiber mat devices—showing A (Control uncrosslinked) and B (Optimized mat).

DSC analysis was conducted to determine the interactions between the various polymers when forming an Interpenetrating Polymer Network. The DSC thermogram of the various films showed a Tg between the range of 28 and 30° C. Glass Transition Temperature may be defined as the change in heat capacity when a transition occurs and can be directly related to network formation and crosslinker concentration. When semi-crystalline materials are present, crystallites within the structure effects the mobility of amorphous regions is influenced by these crystallites and ultimately influences the Tg to shift to a higher concentration, in addition the degree of crosslinkage effect the amorphosicity of the structure and thus it can be seen that the highest Tg is observed in Film 1 (red arrow) and is associated with crosslinkage of the amino groups within the structure that is capable of crosslinking at the temperature of curing. A decrease in crosslinkage due to crosslinker concentrations lower than the optimum as seen in Film 2 (blue arrow) results in a lower Tg, thus is likely to display a quicker onset of degradation. When a polymeric structure reaches the crystalline state more order is maintained and the degree of molecular motion is decreased and this is influenced by factors such as molecular weight distribution and stereoregularity, thus it can be observed from the calibration curves obtained that Film 10 has the highest degree of crystallinity at 213.96° C. and the lowest been 128.79° C. in Film 9 (displayed by black blocks in the Figure). This can be attributed to the low % concentration of polymer been used in Film 10 and a higher % used in Film 9 thus the degree of crosslinkage varies. This suggests that Film 10 displays a greater degree of regular molecular arrangements due to the formation of inter and intramolecular bonds, thus a well-defined structure is obtained. In addition Film 10 also displays the lowest degree of decomposition at a high temp range of 213.96° C. which can further be attributed to its crystalline state (blue circle). Film 9 shows a lower degree of crystallinity and can be related to the random orientation of molecules displaying amorphous behaviour, that can be related to free uncrosslinked groups within the structure with a poor polymer backbone. Furthermore the amorphous form of Film 9 can also be deduced by the lack of a crosslinking (curing) exothermic peak (shown by red circle) proceeding the endothermic melting transition phase present in all films showing semi-crystalline behaviour.

Figure 6A:
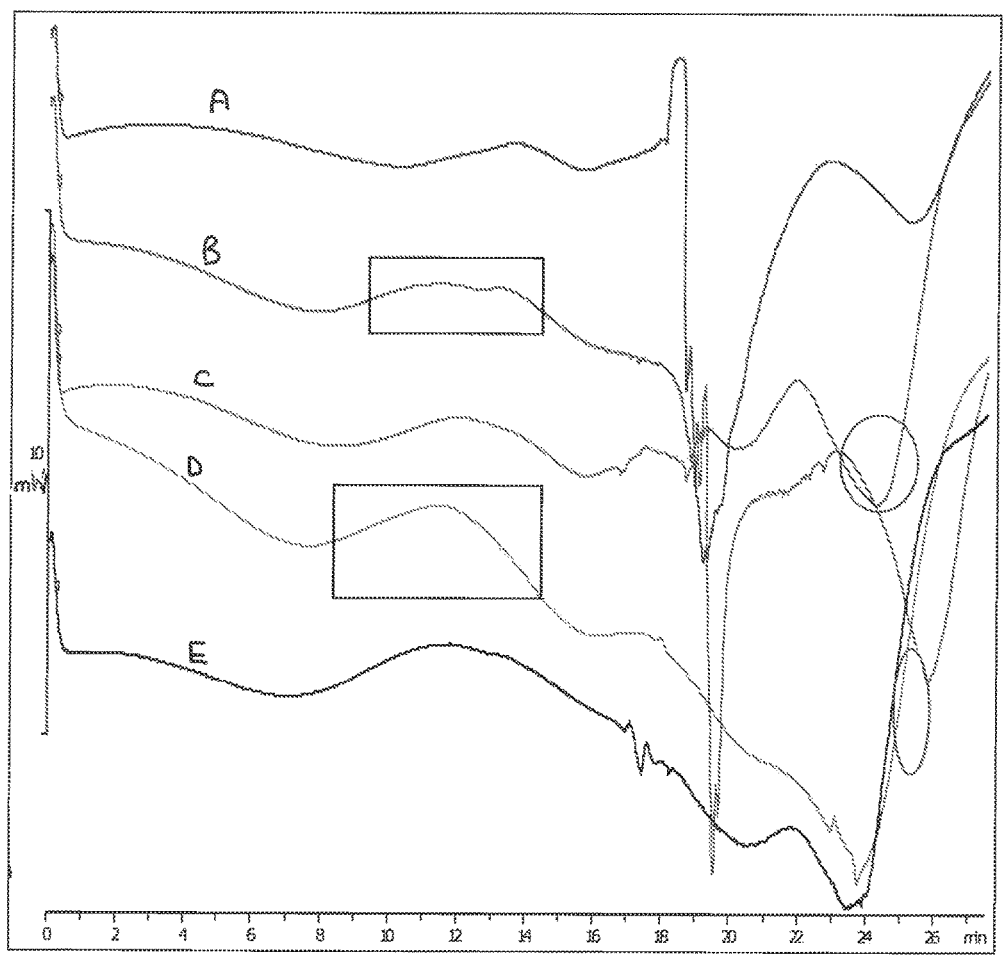
FIG. 6 shows DSC schematic of (a) biofilm devices—showing from top to bottom A (Film 6), B (Film 11), C (Film 3, D (Film 10) and E (Film 2); and (b) electrospun fiber mat devices—from top to bottom A (Control uncrosslinked) and B (Optimized mat)
Figure 6B:
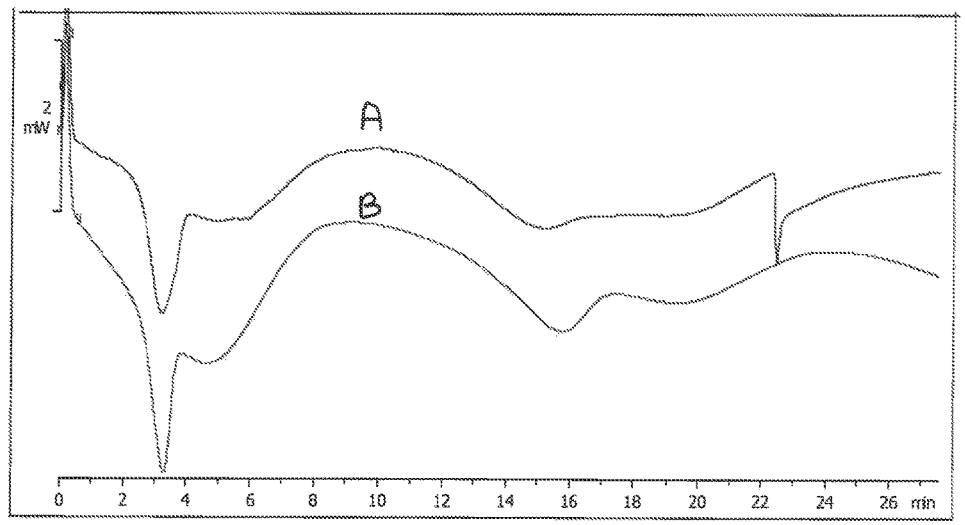

FIG. 6b shows a Tg at 28.21° C., a degredation rate at 258.99° C. and crystalline behaviour at 114.81° C. which is relatively in the same range as the biofilms in FIG. 6a thus suggesting that when placed under thermal conditions both films and nanofibres will behave in a relatively similar pattern.

Characterisation of the Lyophilized Hyaluronic Acid (HA) Hydrogel

Mucoadhesive Properties of the Lyophilized Hyaluronic Acid (HA) Hydrogel

Mucoadhesion can be defined as a polymers or materials ability to adhere or bind to the desired tissue. This is of crucial importance when developing a system for wound healing as topical preparations require favourable application properties to ensure patient compliance and optimal delivery. Furthermore mucoadhesive delivery systems are capable of increasing the bioavailability of the active compounds thus controlling release of the bioactive at the desired site whilst also extending the retentive time (Cevher et al., 2008). A TA-XTplus analyzer equipped with a 5 kg load was employed to evaluate the mucoadhesive properties of the prototype device via attachment to excised Sprague Dawley rat skin. The work of mucoadhesion was evaluated by employment of the following equation:

$$\text{Work of Mucoadhesion}(mJ \cdot cm^{-2}) = \frac{AUC}{\pi r^2} \quad \text{[Equation 1]}$$

Whereby $\pi r^2$: Surface area of the skin tissue which is in contact with the gel formulations.

Figure 7A:
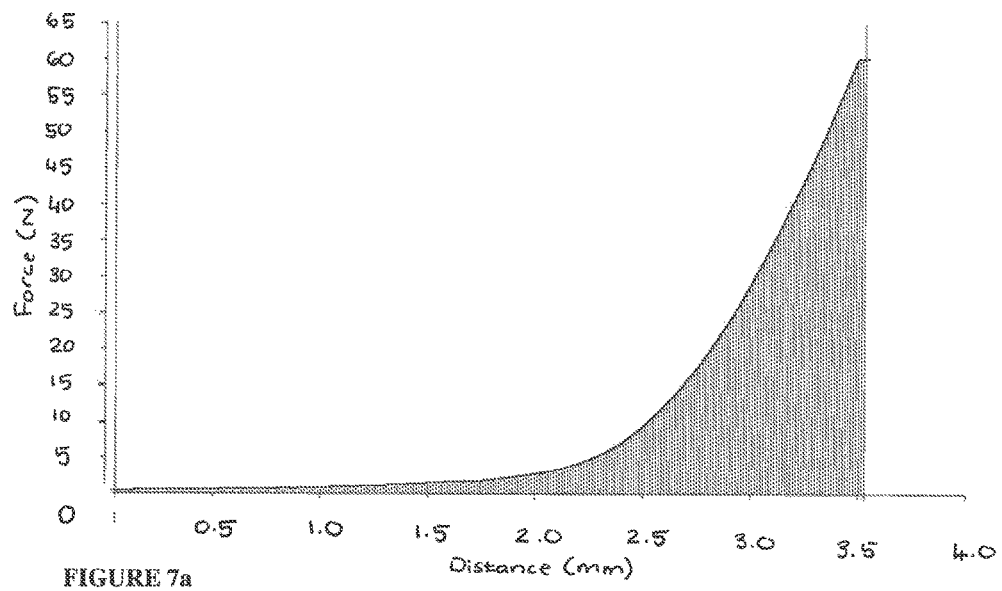
FIG. 7 shows the area under the curve (AUC) for the work of mucoadhesion of the prototype device wherein (a) shows the AUC for the backing layer and (b) shows the AUC for the HA hydrogel.
Figure 7B:
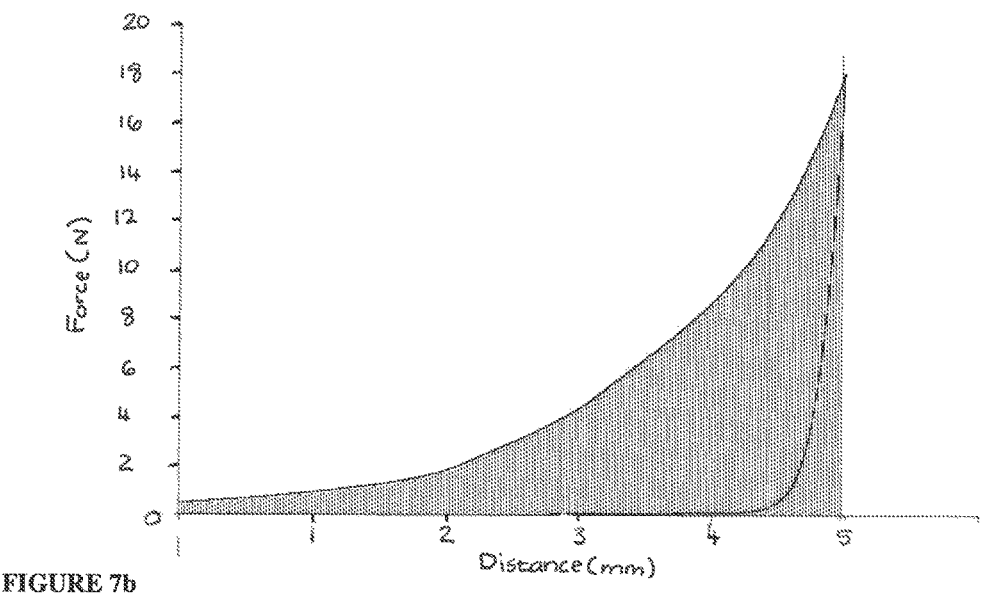

The mucoadhesive tests were carried out to determine the adhesive properties of the formulations for device fabrication. From the work of mucoadhesion obtained the backing layer formulation displayed a value of 0.079 mJcm$^{-2}$ and 0.031 mJcm$^{-2}$ for the lyophilised matrix formulation. Thus the results obtained depict greater adhesive strength of the gel formulation of the backing layer which serves as an ideal prototype for wound healing. This can be directly attributed to the use of a mucoadhesive polymer such as polyacrylic acid. Literature findings suggest that the presence of more than 90% of acidic groups in non ionised polyacrylic acids avert electrostatic charges and thus demonstrate lower swelling abilities thus enhancing its binding properties directly to proteins and polysaccharides found in skin tissue (El-Kamel at al., 2002). FIG. 7 shows the area under the curve (AUC) for the work of mucoadhesion of the prototype device wherein (a) shows the AUC for the backing layer and (b) shows the AUC for the HA hydrogel.

In Vitro Bioactive Release in Response to a Stimulus Inflammation (HA Hydrogel Having Embedded Electrospun Fiber Mats Therein)

Optimized electrospun mat devices were embedded within lyophilized HA hydrogel formulations F1-F15 as described above, following which in vitro bioactive release experiments were conducted The release of bioactive is dependent upon a bio-response. The mechanism involves the release of hydroxyl radicals from the targeted wound site that comes into contact with the lyophilised inflammatory dependent matrix causing degradation of hyaluronic acid present in the matrix which ultimately leads to exposure of the nanofibrous mats. From the results obtained in FIG. 8 it can be seen that the rate of bioactive release is dependent upon the concentration used. When higher concentrations of polymer and crosslinker is used such as that in F2, F4, F9 and F12 the rate of release is lower. This is attributed to chain and bond formation occurring via intermolecular and intramolecular forces formed when crosslinking occurs. Bond formation and conjugation provide a greater resistance to degradation on exposure to hydroxyl radicals. When lower concentrations are used such as that in F5 and F10 bioactive release is greater. Lower concentrations favour easier degradation of the lyophilised matrix on exposure to radicals providing rapid exposure of bioactives to the targeted site. Furthermore the release of bioactives is directly related to the hyaluronic acid available in the matrix as well as the concentrations used. When placed in an aqueus solution hyaluronic acid tends to exhibit a random coil-coil structure with hydrophobic and hydrophilic strands. The bioactive studied for release rate is curcumin and also exhibits hydrophobic properties and thus is released more slowly. Thus the use of hyaluronic acid as a bioresponsive lyophilised inflammatory dependent matrix serves as an excellent potential for controlled bioactive release based on its hydrophobicity properties (Luo et al., 2000) as well as its capacity to respond to a biostimulus which is hydroxyl radicals release during inflammation at the wound site allowing the d4evice to act as a local delivery device at the target site. FIG. 8a-c shows in vitro bioactive release profiles of Formulation 1-15.

Determination of the Tensile and Mechanical Properties of the Lyophilized Hyaluronic Acid (HA) Hydrogel on the Nanometer Scale The tensile and mechanical properties of all formulations were investigated by employing nanotensile analysis. FIG. 9 below depicts the stress-strain profile representing the Youngs Modulus significance of the lyophilised matrix. From the profile obtained the Youngs Modulus is represented by the linear portion of the grapth as indicated and the fracture point is also perceived indicating the maximum strain required to fracture the device. From the results obtained it can be seen that a greater Youngs Modulus is ontained when higher polymeric concentattions are used and in particular sodium alginate. Elevated Youngs Modulus values are seen in F12, F14 and F1 whereby concentrations of 4.5% w/v of alginate is used in F12 and F1 and a greater degree of crosslinkeage occurs in F1 at a crosslinker concentration of 0.13%w/v. The Youngs Modulus obtained was 1.22 E(mPa), 053 E(mPa) and 0.61 E(mPa) respectively. A higher Youngs Modulus value suggest greater rigidity and stiffness to the matrix device. Increasing polymeric concentrations affects the polymer backbone formation and polymer chain flexibility which inevitably have an impact on the stress-strain relationship of the device. The lyophilised matrix device displaying a smaller Youngs Modulus such as in F7 and F11 augment greater flexibility properties. Youngs Modulus values obtained are 0.05 E(mPa) and 0.07 E(mPa). This is due to the low sodium alginate concentrations used at 1%w/v and crosslinker concentrations at 0.1%w/v. Thus for the treatment of wounds and administration of a topical delivery system a prototype device with an intermediate Youngs Modulus is required to provide both strength and flexibility to the system for optimal application. Therefore from the results obtained it can be seen that F5 and F9 will serve as an ideal formulation candidate for device formation as intermediate Youngs Modulus values are obtained thus providing both flexibility and toughness. FIG. 9 depicts a standard stress-strain profile that is obtained upon nanotensile mapping depicting a fracture point and youngs modulus from the graph. The profile depicted however resembles that of Formulation 2 of the HA hydrogel.

CONCLUSIONS

The Applicant believes that the wound dressing according to the invention aids wound healing in all three phases of wound healing and importantly provides a moist environment for wound healing to occur. The Applicant believes that the invention at least ameliorates the disadvantages known in the prior art.

While the invention has been described in detail with respect to specific embodiments and/or examples thereof, it will be appreciated that those skilled in the art, upon attaining an understanding of the foregoing may readily conceive of alterations to, variations of and equivalents to these embodiments. Accordingly, the scope of the present invention should be assessed as that of the claims and any equivalents thereto, which claims are appended hereto.

REFERENCES

1. Sung H. W, Hsincha T. W, Tu H. 2003. Drug loaded biological material chemically treated with genipin. U.S. Pat. No. 6,624,138 BH.
2. Huang Z. M, Zhang Y. Z, Kotaki M, Ramakrishna S. 2003. A review on polymer nanofibres by electrospinning and their applications in nanocomposites. Composite Science and Technology, 63, 2223-2253.
3. Norris I. D, Shaker M. M, Ko F. K, MacDiarmid A. G. 2000. Electrostatic fabrication of ultrafine conducting fibres: polyaniline/polyethylene oxide blends. Synthetic materials, 114, 109-114.
4. Shaluman K. T, Binulal N. S, Selvamurugan N, Nair S. V, Menon D, Furuike T, Tamura H, Jayakumar R. 2009. electrospinning of carboxymethyl chitin/poly (vinyl alcohol) nanofibrous scaffolds for tissue engineering applications, Carbohydrate polymers, 77, 863-869.
5. Rho K. S, Jeong L, Lee G, Seo B. M, Park Y. J, Hong S. D, Rho S, Cho J. J, Park W. H, Min B. M. 2006. Electrospinning of collagen fibres, effects on the behaviour of normal human keratinocytes and early stage wound healing. Biomaterial, 27, 1452-1461.
6. Jalili R, Morshed M, Ravandi S. A. H. 2006. Fundamental parameters affecting electrospinning of PAN nanofibres as uniaxially aligned fibres. Journal of applied polymer science. 101, 6, 4350-4357.
7. Mercandetti M. 2011. Wound Healing and Repair. Medscape Reference: Drug disease and Procedures, an overview-1298129.
8. Boatang J. S., Matthews K. H., Stevens H. N. E., Eccleston G. M. 2007. Wound Healing Dressings and Drug Delivery Systems, A review. Journal of Pharmaceutical Sciences. 97, (8), 2892-2900.
8. Charernsriwilaiwat N., Opanasopit P., Rojanarata T., Ngawhirunpat T., 2012. Lysozyme loaded electrospun chitosan based nanofibre mats for wound healing. International Journal of Pharmaceutics, 1-6.
9. Dou M., Xiu-Ling, Xu Xu, Kong X. Y., Yi Li X., Guo G., Luo F., Zhao X., Wei Y. Q., Qian Z., 2009. Chitosan-Alginate Sponge, Preparation and Application in curcumin delivery for dermal wound healing in rats. Journal of Biomedicine and Biotechnology, 2009, ID: 595126, 8.
10. Akhilender K., 2003. Vitamin C in Human Health and Disease, Nutritional Journal Review, 2, 7.
11. Banarjee S., 2010. Interpenetrating Polymer Network (IPN), Novel Biomaterial, Review Article. International Journal of Pharmaceutics.2 (1), 28-30.
12. Zagris N. 2001, Extracellular matrix in development of the early embryo. Micron, 32, 4, 427-38. [Pub Med: 11070362]
13. Goldberg M, Langer R, Xinqiao J, 2007. Nanostructured materials for applications in drug delivery and tissue engineering. J Biomater Sci Polym Ed. 18(3), 241-268.
14. Datta H. S, Mitra S. K, and Patwardhan B. 2011. Wound Healing Activity of Topical Application Forms Based on Ayurvedav, Evid Based Complement Alternat Med. 2011; 2011: 134378.
15. Topham J. 2002. Why do some cavity wounds treated with honey or sugar paste heal without scarring?, Journal of wound care, 11, 2, 53-5.
16. Bhardwaj N, Kundu S. C. 2010. Electrospinning: A fascinating fibre fabrication technique. Research Review Paper. Biotechnology Advances. 28, 325-347.
17. Singla A. K and Chawla M, 2001. Chitosan: some pharmaceutical and biological aspects—an update, Review Article. Journal of Pharmacy and Pharmacology, 53,1047-1067
18. Bigi A, Cojazzi G, Panzavolta S, Roveri N, Rubini K. 2002. Stabilisation of gelatin films by crosslinking with Genipin. Biomaterials, 23, 4827-4832
19. Luo Y, Kirker K R, Prestwich G D. 2000. Cross-linked hyaluronic acid hydrogel films: new biomaterials for drug delivery. Journal of Controlled Release 69, 169-184
20. The Lancet (2003) Lancet 362:673
21. Jeong B, Gutowska A (2002) Trends Biotechnol 20:305-311
22. Hoffman A S, Stayton P S, Bulmus V, Chen G, Chen J, CheungC, Chilkoti A, Ding Z, Dong L, Fong R, Lackey C A, Long C J, Miura M, Morris J E, Murthy N, Nabeshima Y, Park T G, Press O W, Shimoboji T, Shoemaker S, Yang H J, Monji N, Nowinski R C, Cole C A, Priest J H, Harris J M, Nakamae K, Nishino T, Miyata T (2000) J Biomed Mater Res 52:577-586
23. Kikuchi A, Okano T (2002) Prog Polym Sci 27:1165-1193
24. Cabane E, Zhang X, Langowska K, Palivan C G, Meier W. 2012. IN FOCUS: NANOMEDICINE—REVIEW Stimuli-Responsive Polymers and Their Applications in Nanomedicine. Biointerfaces. 7-9
25. Gathin G., 2007. The significance of surface pH in chronic wounds. Wounds UK, Wound Healing Science, 3, 3, 53-56.
26. Li X, Chen S, Zhang B, Li M, Diao K, Zhang Z, Li J, Xu Y, Wang X, Chen H., 2012. In situ injectable nanocomposite hydrogel composed of curcumin, N,O-carboxymethyl chitosan and oxidized alginate for wound healing application. International Journal of Pharmaceutics, pharmaceutical nanotechnology.
27. Stuart M. A. C, Huck W. T. S, Genzer J, Müller M, Ober C, Stamm M, Sukhorukov G. B, Szleifer I, Tsukruk V. V, 27. Urban M, Winnik F, Zauscher S, Luzinov I and Minko S., 2010. Emerging applications of stimuli responsive polymer materials. Nature materials. 9, 101-113.
28. Alvarez-Lorenzo C, Concheiro A., 2004. Molecularly imprinted polymers for drug delivery. J Chrom B, 804,1, 231-245.
29. Singer A. J, Clark R. A. F., 1999. Cutaneous wound healing, mechanism of disease, Review Article. The New England Journal of Medicine 341: 10: 738-746.
30. Darzynkiewic Z and Balazr E. W., 1971. Effect of connective tissue intercellular matrix on lymphocyte stimulation, Exp. Cell Res. 66, 113-123.
31. Howling G I, Dettmor P N, Goddard P A, Hampson F C, Dornish M, Wood A J. 2001. The effect of chitin and chitosan on the proliferation of human skin fibroblasts and keratinocytes in vitro. Biomaterials. 2959-66.
32. Ishihara M, Nakanishi K, Ono K, Sato M, Kikuchi M, Saito Y. 2002. Photocrosslinkable chitosan as addressing for wound occlusion and acceleration in healing processes. Biomaterials. 23, 833-840.
33. Alemdaroglu C, Degim Z, Celebi N, Zor F, Ozturk S, Erdogen D. 2006. An investigation on burn wound healing in rats with chitosan gels formulation containing epidermal growth factor. Burns. 32, 319-327.
34. Mi F L, Sung H W, Shyu S S., 2002. Drug release from chitosan-alginate complex beads reinforced by a naturally occurring cross-linking agent. Carbohydrate Polymers. 48, 1, 61-72.
35. Muzarelli R A. 2009. A genipin crosslinked chitosan hydrogel as biomedical and pharmaceutical airs. Review. Carbohydrate Polymers. 77, 1-9.
36. Nagoba B S, Gandhi R C, Wadner B J, Rao A K, Hortalkar A R, Selkas S P. 2010. A simple and effective approach for the treatment of diabetic foot ulcers with different wagner grades. International Wound Journal. 7, 153-158.
37. Topham J. 2002. Why do some cavity wounds treated with honey or sugar paste heal without scarring? Journal of wound care. 11,2,53-5.
38. Braund R, Tucker I G, Medlicitt N J. 2007. Hypromellose films for the delivery of growth factors for wound healing. Journal of Pharmacy and Pharmacology. 59, 367-372
39. Pachence J M. 1996. Collagen based device for soft tissue repair. J Biomed Mater Res (Appl Biomaterial). 33, 35-40.
40. Gopinath D, Ahmed M R, Gomathi K, Chitra K, Srhgal P K, Jayakumar R. 2004. Dermal wound healing processes with curcumin incorporated collagen films. Biomaterials. 25, 1911-1917.
41. Anilkumar T. V, Muhameda J, Jose A, Mohanan P. V, Lissy K, Krishnan L. K., 2011. Advantages of hyaluronic acid as a component of fibrin sheet for care of acute Wound Biologicals 39, 81-88
42. Perttila J, Salo M, Peltola O., 1990. Plasma fibronectin concentrations in blood products. Intensive Care Med. 16,41e3.
43. Gutteridge J. M. C and Wilkes S., 1983. Copper salt dependent hydroxyl radical formation damage to proteins acting as antioxidant, Biochim. Biophyr. Acta 759, 38-41.
44. Yui N, Nihira J, Okano T, Sakurai Y., 1992. Inflammation responsive degradation of crosslinked hyaluronic acid gels. J Contr Rel. 22,105-116.
45. Balakrishnan B, Mohanty M, Umashankar P. R, Jayakrishnan A., 2005. Evaluation of an in situ forming hydrogel wound dressing based on oxidized alginate and gelatin. Biomaterials 26, 6335-6342.
46. Thu H-E, Zulfakar M. H, Shiow-Fern N., 2012. Alginate based bilayer hydrocolloid films as potential slow-release modern wound dressing. International Journal of Pharmaceutics 434, 375-383
47. Lloyd L. L, Kennedya J. F, Methacanona P, Paterson M, Knill C. J., 1998. Carbohydrate polymers as wound management aids. Carbohydrate Polymers 37,315-322
48. Zhao Q S, Ji Q X, Xing K, Li X Y, Liu C S, Chen X G. Preparation and characteristics of novel porous hydrogel films based on chitosan and glycerophosphate, Carbohydrate Polymers. 2009; 76 :410-416
49. Bhuvaneshwari S, Sruthi D, Sivasubramanian V, Niranjana K, Sugunabai J. Development and characterization of chitosan films. International Journal of Engineering Research and Applications (IJERA). 2000; 1:2:292-299
50. Chong E J, Phan T T, Lim I J, Zhang Y Z, Bay B H, Ramakrishna S, Lim C T. 2007. Evaluation of electrospun PCL/gelatin nanofibrous scaffold for wound healing and layered dermal reconstitution. Acta Biomaterialia 3, 321-330
51. Haghi A K, Akbari M. 2007. Trends in electrospinning of natural nanofibres. Phys stat sol (a). 204, 6, 1830-1834
52. Pham Q P, Sharma U, Mikos A G. 2006. Electrospinning of Polymeric Nanofibers for Tissue Engineering Applications: A Review. Tissue engineering 12, 5
53. Shaikh R P, Kumar P, Choonara Y E, du Toit L C Pillay V. 2012. Crosslinked electrospun PVA nanofibrous membranes: elucidation of their physicochemical, physicomechanical and molecular disposition. Biofabrication 4, 025002, 21pp
54. El-Kamel A, Sokar M, Naggar V, Gamal S A. 2002. Chitosan and sodium alginate-based bioadhesive vaginal tablets. AAPS Pharm Sci. 4:44
55. Cevher E, Sensoy D, Taha M A M, Araman A. 2008. Effect of Thiolated Polymers to Textural and Mucoadhesive Properties of Vaginal Gel Formulations Prepared with Polycarbophil and Chitosan. AAPS Pharm Sci Tech 9, 3

The invention claimed is:

1. A stimuli responsive wound dressing for application against a wound site of a human or animal body, the wound dressing comprising:
a lyophilized hyaluronic acid (HA) hydrogel; and
a plurality of devices embedded within said lyophilized hyaluronic acid hydrogel, each device including chitosan and hypromellose,
wherein said lyophilized hyaluronic acid hydrogel depolymerizes upon contact with hydroxyl radicals from an inflammatory response present at the wound site in order to release the plurality of embedded devices into the wound site, and
wherein said lyophilized hyaluronic acid hydrogel absorbs water and/or exudates facilitating the maintenance of a moist wound site which promotes angiogenesis and wound healing.

2. The wound dressing according to claim 1, wherein the lyophilized hyaluronic acid hydrogel further comprises alginate, the alginate in use absorbs water and/or exudates facilitating the maintenance of a moist wound site which promotes angiogenesis and wound healing.

3. The wound dressing according to claim 2, wherein the alginate is sodium alginate.

4. The wound dressing according to claim 1, wherein the lyophilized hyaluronic acid hydrogel further comprises a first crosslinking agent selected from the group consisting of adipic dihydrazide (ADH), dithiobis(propanoic dihydrazide) (DTP), dithiobis(butyric dihydrazide) (DTB), tyrosine and tyrosine hydrazide.

5. The wound dressing according to claim 4, wherein the first crosslinking agent is adipic dihydrazide (ADH).

6. The wound dressing according to claim 1, wherein each of the plurality of devices further comprises at least one active pharmaceutical ingredient (API) selected from the group consisting of curcumin, farnesol, benzoic acid, eugenol, cinnamic acid, *Thymus vulgaris* (thyme) extract, *Rosmarimus officinalis* (rosemary) extract, *Syzygyum joabolanum* (jambolan) extract, and *Salvia officinalis* (sage) extract.

7. The wound dressing according to claim 6 wherein, the API is curcumin.

8. The wound dressing according to claim 1, wherein each of the plurality of devices further comprises at least one second crosslinking agent selected from the group consisting of iridoid compounds and derivatives of iridoid compounds.

9. The wound dressing according to claim 8, wherein the second crosslinking agent is genipin and/or chromium ascorbate.

10. The wound dressing according to claim 1, wherein each of the plurality of devices further comprises citric acid.

11. The wound dressing according to claim 1, wherein the devices are formed to be biofilms and/or electrospun fiber mats.

12. The wound dressing according to claim 11, wherein the devices are formed as biofilms, and wherein the biofilms further comprise glycerine.

13. The wound dressing according to claim 11, wherein the devices are formed as electrospun fiber mats, and wherein the electrospun fiber mats further comprise at least one member selected from the group consisting of polyethylene oxide (PEO), polyvinyl chloride (PVA) and Tween 80.

14. The wound dressing according to claim 1, further comprising a backing layer upon which the lyophilized hyaluronic acid (HA) hydrogel is layered so as to form a bi-layered wound dressing, in use, the backing layer faces away from the wound site and facilitates unidirectional release of the plurality of devices.

15. The wound dressing according to claim 14, wherein the backing layer is a hydrogel formulation comprising alginate and/or polyacrylic acid.

16. The wound dressing according to claim 15, wherein the backing layer further comprises a plasticizer, and/or an anti-foaming agent.

* * * * *